(12) United States Patent
Michalak et al.

(10) Patent No.: US 7,709,661 B2
(45) Date of Patent: May 4, 2010

(54) SYNTHETIC METHODOLOGY FOR THE REDUCTIVE ALKYLATION AT THE C-3 POSITION OF INDOLES

(75) Inventors: Ronald S. Michalak, Congers, NY (US); Panolil Raveendranath, Monroe, NY (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 11/872,193

(22) Filed: Oct. 15, 2007

(65) Prior Publication Data

US 2008/0161581 A1 Jul. 3, 2008

Related U.S. Application Data

(63) Continuation of application No. 11/014,657, filed on Dec. 16, 2004, now Pat. No. 7,282,594.

(60) Provisional application No. 60/529,797, filed on Dec. 16, 2003.

(51) Int. Cl.
C07D 209/14 (2006.01)
(52) U.S. Cl. .................................. 548/506
(58) Field of Classification Search ............ 548/506
See application file for complete search history.

(56) References Cited

U.S. PATENT DOCUMENTS

| | | | |
|---|---|---|---|
| 6,306,852 B1 | 10/2001 | Rawson et al. |
| 6,635,771 B2 | 10/2003 | McKew et al. |
| 6,797,708 B2 | 9/2004 | McKew et al. |
| 6,891,065 B2 | 5/2005 | Wu et al. |
| 6,984,735 B2 | 1/2006 | McKew et al. |
| 7,557,135 B2 | 7/2009 | McKew et al. |
| 2003/0144282 A1 | 7/2003 | McKew et al. |
| 2003/0149029 A1 | 8/2003 | McKew et al. |
| 2003/0158405 A1 | 8/2003 | McKew et al. |
| 2003/0166649 A1 | 9/2003 | McKew et al. |
| 2004/0082785 A1 | 4/2004 | McKew et al. |
| 2005/0020858 A1 | 1/2005 | Wu et al. |
| 2005/0049296 A1 | 3/2005 | Dehnhardt |
| 2005/0070723 A1 | 3/2005 | Dehnhardt et al. |
| 2005/0159613 A1 | 7/2005 | Wu et al. |
| 2006/0014759 A1 | 1/2006 | McKew et al. |
| 2006/0041005 A1 | 2/2006 | Michalak et al. |
| 2007/0004719 A1 | 1/2007 | McKew et al. |

FOREIGN PATENT DOCUMENTS

| | | |
|---|---|---|
| WO | WO 95/06046 | 3/1995 |
| WO | WO 2005/012238 | 2/2005 |
| WO | WO2006/128142 | 11/2006 |

OTHER PUBLICATIONS

Mahadevan et al., *Tetrahedron Letters*, published Jun. 9, 2003, 44, 4589-4591.
Comprehensive Organic Chemistry (1979) 4(17) "Indoles and Related Systems."
Greene et al., "Protective Groups in Organic Synthesis" 3$^{rd}$ ed., John Wiley & Sons 1999.
Appleton et al., "A mild and selective C-3 reductive alkylation of indoles," *Tetrahedron Letters* (1993) 1529-1532.
International Search Report dated May 11, 2005 for International Application No. PCT/US2004/041989.

*Primary Examiner*—Rebecca L Anderson
*Assistant Examiner*—Jason M Nolan
(74) *Attorney, Agent, or Firm*—Thomas C. McKenzie

(57) ABSTRACT

A process for the reductive alkylation at the C-3 position of an indole compound in which the indole is treated with an aldehyde in the presence of a Lewis acid and a silicon hydride reducing agent. The process is useful for alkylating the C-3 position of indoles that contain acid-sensitive substituents at the N-1 position.

1 Claim, No Drawings

SYNTHETIC METHODOLOGY FOR THE REDUCTIVE ALKYLATION AT THE C-3 POSITION OF INDOLES

CROSS REFERENCE TO RELATED APPLICATIONS

The present application is a continuation of U.S. application Ser. No. 11/014,657, filed on Dec. 16, 2004 now U.S. Pat. No. 7,282,594, which claims the benefit under 35 U.S.C. § 119(e) to Provisional Application Ser. No. 60/529,797, filed Dec. 16, 2003; each of these prior filed applications is incorporated herein by reference in its entirety.

FIELD OF THE INVENTION

This invention relates to synthetic methodology for the reductive alkylation at the C-3 position of indoles.

BACKGROUND

C-3 alkylation of indoles in general is a facile process, as shown in Comprehensive Organic Chemistry, 1979, V. 4, Chapter 17, "Indoles and Related Systems". This alkylation can occur under basic or acidic reaction conditions. The effect of different metal cations, base concentration, and catalysts for the phase transfer alkylation of indoles under basic conditions has been studied. Alkylation of indoles under acidic reaction conditions can often proceed with catalytic amounts of acid catalysts. An examination of the literature reveals a large number of acid catalysts that have been used for the C-3 alkylation of indoles.

It is convenient to achieve both alkylation and reduction transformations simultaneously when indoles with C-3 saturated substituents are desired. Triethylsilane is a convenient reducing agent under acidic reaction conditions, and trifluoroacetic acid and triethylsilane have been used as a reagent combination to accomplish simultaneous alkylation and reduction at the C-3 position of indoles; Steele, et al. Tet Lett 1993, p 1529. Unfortunately, trifluoroacetic acid is incompatible with some acid sensitive functional groups, and, in fact, trifluoroacetic acid is well known as a reagent for the cleavage of benzhydryl protecting groups; Greene and Wuts, "Protective Groups in Organic Synthesis" 3$^{rd}$ ed., John Wiley & Sons, 1999.

SUMMARY

The present invention comprises a process for the reductive alkylation at the C-3 position of an indole compound, the process comprising treating the indole with an aldehyde in the presence of a Lewis acid and a silicon hydride reducing agent. The process is particularly useful for alkylating the C-3 position of indoles that contain acid-sensitive substituents at the N-1 position.

In particular embodiments, the indole has the formula

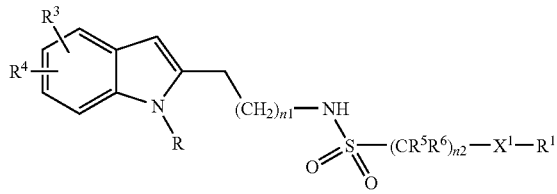

wherein the variables R, $R^1$, $R^3$, $R^4$, $R^5$, $R^6$, $X^1$, $n_1$, and $n_2$ are defined as described herein. Acid-sensitive groups that may be present at the N-1 position of the indole include, for example, those having the formula

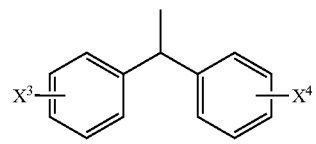

wherein $X^3$ and $X^4$ are defined as described herein. Particular examples of acid-sensitive groups include, for example, benzhydryl, 2,4-dimethoxybenzyl, 2-hydroxybenzyl, 5-dibenzosuberyl, triphenylmethyl, and the like.

DETAILED DESCRIPTION

Methods of the present invention for the reductive alkylation at the C-3 position of an indole compound comprise treating the indole with an aldehyde in the presence of a Lewis acid and a silicon hydride reducing agent. The methods are particularly useful for alkylating the C-3 position of indoles that contain acid-sensitive substituents at the N-1 position.

Suitable silicon hydride reducing agents include, for example, phenylmethylsilane, diphenylsilane, triphenylsilane, and tri($C_1$-$C_4$ alkyl)silanes, such as trimethylsilane and triethylsilane. Suitable Lewis acids include salts comprising a cation selected from boron, aluminum, antimony and rare earth metals such as scandium or lanthanum, particularly in combination with a halogen or triflate anion. Other suitable Lewis acids include pentafluorophenylmetallic acids in which the metal is boron, aluminum, antimony or a rare earth metal. Preferably, the Lewis acid comprises a fluoride, chloride, or triflate salt of boron, aluminum, antimony or a rare earth metal, and/or comprises pentafluorophenylboronic acid. Examples of suitable Lewis acids include, for example, boron trifluoride ($BF_3$), boron tris(trifluoromethanesulfonate), aluminum trichloride ($AlCl_3$), aluminum trifluoride ($AlF_3$), pentafluorophenylboronic acid, and lanthanum trifluoromethanesulfonate.

In some embodiments, after the reaction has begun (i.e. after combination of the indole, aldehyde, silicon hydride reducing agent, and the Lewis acid) a suitable organic acid, e.g., trifluoroacetic acid, $CCl_xH_{3-x}CO_2H$ (where X is 0-3), or an aryl sulfonic acid (e.g., p-toluenesulfonic acid or benzenesulfonic acid) may be added to the reaction mixture to increase the rate of conversion of the reactants to the final product. The organic acid may be added some time after the reaction has begun, for example, approximately 30-60 minutes after the reaction has begun. The reaction is preferably conducted at a temperature in the range of approximately −30° C. to +25° C.

Embodiments of the invention include those where the indole has the formula

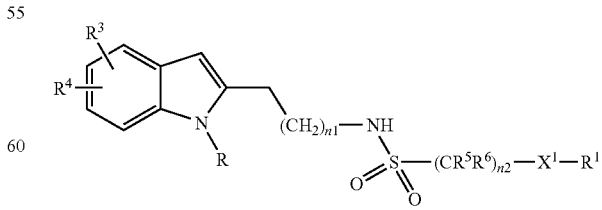

wherein

R is selected from the group consisting of —$(CH_2)_{n3}$-A, —$(CH_2)_{n3}$—S-A, and —$(CH_2)_{n3}$—O-A, wherein A is selected from the group consisting of:

wherein

E is selected from the group consisting of H, $C_1$-$C_6$ alkyl, $C_1$-$C_6$ alkoxy, —$CF_3$, and —$(CH_2)_{n4}$—$CF_3$; and D and G independently are selected from the group consisting of phenyl, pyridinyl, pyrimidinyl, furyl, thienyl and pyrrolyl, each optionally substituted by from 1 to 3, preferably 1 to 2, substituents selected independently from H, halogen, —CN, —CHO, —$CF_3$, —$OCF_3$, —OH, —$C_1$-$C_6$ alkyl, $C_1$-$C_6$ alkoxy, —$NH_2$, —$N(C_1$-$C_6$ alkyl$)_2$, —NH($C_1$-$C_6$ alkyl), —NH—C(O)—($C_1$-$C_6$ alkyl), —$NO_2$, and a 5- or 6-membered heterocyclic or heteroaromatic ring containing 1 or 2 heteroatoms selected from O, N or S;

$X^1$ is selected from the group consisting of a chemical bond, —S—, —O—, —S(O)—, —S(O)$_2$—, —NH—, —NHC(O)—, —C=C—,

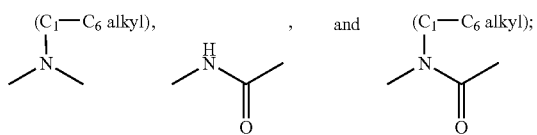

$R^1$ is selected from the group consisting of $C_1$-$C_6$ alkyl, $C_1$-$C_6$ fluorinated alkyl, $C_3$-$C_6$ cycloalkyl, tetrahydropyranyl, camphoryl, adamantyl, CN, —N($C_1$-$C_6$ alkyl)$_2$, phenyl, pyridinyl, pyrimidinyl, furyl, thienyl, napthyl, morpholinyl, triazolyl, pyrazolyl, piperidinyl, pyrrolidinyl, imidazolyl, piperizinyl, thiazolidinyl, thiomorpholinyl, tetrazole, indole, benzoxazole, benzofuran, imidazolidine-2-thione, 7,7,dimethyl-bicyclo[2.2.1]heptan-2-one, benzo[1,2,5]oxadiazole, 2-oxa-5-aza-bicyclo[2.2.1]heptane, piperazin-2-one and pyrrolyl, each optionally substituted with 1 to 3 substituents independently selected from the group consisting of H, halogen, —CN, —CHO, —$CF_3$, —$OCF_3$—OH, $C_1$-$C_6$ alkyl, —($C_1$-$C_6$ alkyl)-$R^7$, $C_1$-$C_6$ alkoxy, —($C_1$-$C_6$ alkoxy)-$R^7$, —C(O)—($C_1$-$C_6$ alkyl), —$NH_2$, —N($C_1$-$C_6$ alkyl)$_2$, —NH($C_1$-$C_6$ alkyl), —($C_1$-$C_6$ alkyl)-$NH_2$, —($C_1$-$C_6$ alkyl)-N($C_1$-$C_6$ alkyl)$_2$, —($C_1$-$C_6$ alkyl)-NH($C_1$-$C_6$ alkyl), —NH—C(O)—($C_1$-$C_6$ alkyl), —$NO_2$, —$SO_2$($C_1$-$C_6$ alkyl), —$SO_2NH_2$, —$SO_2NH$($C_1$-$C_6$ alkyl), —$SO_2N$($C_1$-$C_6$ alkyl)$_2$, —COOH, —C(O)O—($C_1$-$C_6$ alkyl), —($C_1$-$C_6$ alkyl)-COOH, 1-chloro-2-methyl-propyl, —$C_1$-$C_6$ thioalkyl, —($C_1$-$C_6$ alkyl)C(O)$CH_3$, —($C_1$-$C_6$ alkyl)O$CH_3$, C(O)$NH_2$, phenyl, benzyl, benzyloxy, morpholino, pyrrolidino, piperidine, piperizine, furan, thiophene, imidazole, tetrazole, pyrazine, pyrazolone, pyrazole, imidazole, oxazole, isoxazole, thiazole, 2-methyl-thiazole,

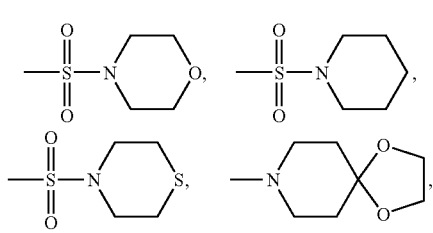

-continued

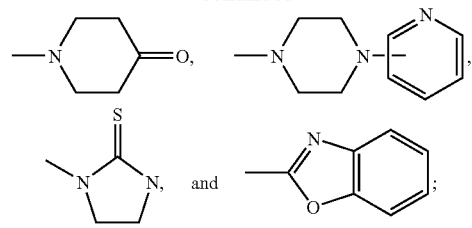

$R^3$ is selected from the group consisting of H, halogen, —CN, —CHO, —$CF_3$, —$OCF_3$, —OH, —$C_1$-$C_6$ alkyl, $C_1$-$C_6$ alkoxy, $C_1$-$C_6$ thioalkyl, —$NH_2$, —N($C_1$-$C_6$ alkyl)$_2$, —NH($C_1$-$C_6$ alkyl), —NH—C(O)—($C_1$-$C_6$ alkyl), and —$NO_2$;

$R^4$ is selected from the group consisting of H, halogen, —CN, —CHO, —$CF_3$, —$OCF_3$, —OH, —$C_1$-$C_6$ alkyl, $C_1$-$C_6$ alkoxy, $C_1$-$C_6$ thioalkyl, —$NH_2$, —N($C_1$-$C_6$ alkyl)$_2$, —NH($C_1$-$C_6$ alkyl), —NH—C(O)—($C_1$-$C_6$ alkyl), —$NO_2$, —NH—C(O)—NH($C_1$-$C_6$ alkyl)$_2$, —NH—C(O)—NH($C_1$-$C_6$ alkyl), —NH—C(O)—O—($C_1$-$C_6$ alkyl), —$SO_2$—($C_1$-$C_6$ alkyl), —S—($C_3$-$C_6$ cycloalkyl), —S—$CH_2$—($C_3$-$C_6$ cycloalkyl), —$SO_2$—($C_3$-$C_6$ cycloalkyl), —$SO_2$—$CH_2$—($C_3$-$C_6$ cycloalkyl), $C_3$-$C_6$ cycloalkyl, —$CH_2$—($C_3$-$C_6$ cycloalkyl), —O—($C_3$-$C_6$ cycloalkyl), —O—$CH_2$—($C_3$-$C_6$ cycloalkyl), phenyl, benzyl, benzyloxy, morpholino, pyrrolidino, piperidine, piperizine furan, thiophene, imidazole, tetrazole, pyrazine, pyrazolone, pyrazole, imidazole, oxazole and isoxazole, the rings of each of these $R_4$ groups each being optionally substituted by from 1 to 3 substituents selected from the group consisting of H, halogen, —CN, —CHO, —$CF_3$, —OH, $C_1$-$C_6$ alkyl, $C_1$-$C_6$ alkoxy, —$NH_2$, —N($C_1$-$C_6$ alkyl)$_2$, —NH($C_1$-$C_6$ alkyl), —NH—C(O)—($C_1$-$C_6$ alkyl), —$NO_2$, —$SO_2$($C_1$-$C_6$ alkyl), —$SO_2NH$($C_1$-$C_6$ alkyl), —$SO_2N$($C_1$-$C_6$ alkyl)$_2$, and —$OCF_3$;

$R^5$ and $R^6$ independently are selected from the group consisting of H and $C_1$-$C_6$ alkyl;

alternatively, $R^5$ and $R^6$ together with the atom to which they are bonded form $C_3$-$C_6$ cycloalkyl;

$R^7$ is selected from the group consisting of phenyl, benzyl, benzyloxy, morpholino, pyrrolidino, piperidine, piperizine, furan, thiophene, imidazole, tetrazole, pyrazine, pyrazolone, pyrazole, imidazole, oxazole, isoxazole, thiazole, 2-methyl-thiazole, each being optionally substituted by from 1 to 3 substituents selected from the group consisting of H, halogen, —CN, —CHO, —$CF_3$, —OH, —$C_1$-$C_6$ alkyl, $C_1$-$C_6$ alkoxy, —C(O)—($C_1$-$C_6$ alkyl), —C(O)O—($C_1$-$C_6$ alkyl), —$NH_2$, —N($C_1$-$C_6$ alkyl)$_2$, —NH($C_1$-$C_6$ alkyl), —NH—C(O)—($C_1$-$C_6$ alkyl), —$NO_2$, —$SO_2$($C_1$-$C_6$ alkyl), —$SO_2NH$($C_1$-$C_6$ alkyl), —$SO_2N$($C_1$-$C_6$ alkyl)$_2$, and $OCF_3$;

$n_1$ is an integer selected from 1, 2, or 3;

$n_2$ is an integer selected from 0, 1, 2, 3, or 4;

$n_3$ is an integer selected from 0, 1, 2, or 3; and $n_4$ is an integer selected from 1, 2, or 3.

It will be understood that the $C_1$-$C_6$ fluorinated alkyl groups in the definition of $R^1$ may be any alkyl group of 1 to 6 carbon atoms with any amount of fluorine substitution including, but not limited to, —$CF_3$, alkyl chains of 1 to 6 carbon atoms terminated by a trifluoromethyl group, —$CF_2CF_3$, etc.

In the definition of $X_1$, the alkenyl bridging group —C=C— is understood to indicate either the cis or trans orientation of the indicated compound(s).

Acid-sensitive groups that may be present at the N-1 position of the indole include, for example, those having the formula

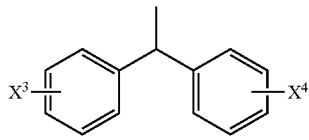

wherein $X^3$ and $X^4$ independently are selected form the group consisting of H, halogen, —CN, —CHO, —CF$_3$, —OCF$_3$, —OH, —C$_1$-C$_6$ alkyl, C$_1$-C$_6$ alkoxy, —NH$_2$, —N(C$_1$-C$_6$ alkyl)$_2$, —NH(C$_1$-C$_6$ alkyl), —NH—C(O)—(C$_1$-C$_6$ alkyl), and —NO$_2$. A particular example of an acid-sensitive group is benzhydryl (i.e., wherein $X^3$ is H and $X^4$ is H).

Other examples of acid-sensitive groups include, for example, 2,4-dimethoxybenzyl, 2-hydroxybenzyl, 5-dibenzosuberyl, triphenylmethyl, and the like, each optionally substituted with 1 to 3, preferably 1 to 2, substituents selected independently from H, halogen, —CN, —CHO, —CF$_3$, —OCF$_3$, —OH, —C$_1$-C$_6$ alkyl, C$_1$-C$_6$ alkoxy, —NH$_2$, —N(C$_1$-C$_6$ alkyl)$_2$, —NH(C$_1$-C$_6$ alkyl), —NH—C(O)—(C$_1$-C$_6$ alkyl), and —NO$_2$.

In particular embodiments, the indole has the structure

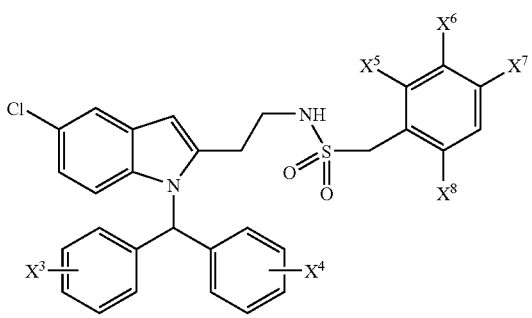

wherein $X^3$ and $X^4$ independently are selected from the group consisting of H, halogen, —CN, —CHO, —CF$_3$, —OCF$_3$, —OH, C$_1$-C$_6$ alkyl, C$_1$-C$_6$ alkoxy, —NH$_2$, —N(C$_1$-C$_6$ alkyl)$_2$, —NH(C$_1$-C$_6$ alkyl), —NH—C(O)—(C$_1$-C$_6$ alkyl), and —NO$_2$; and $X^5$, $X^6$, $X^7$, and $X^8$ independently are selected from the group consisting of H, halogen, —CN, —CHO, —CF$_3$, —OCF$_3$, —OH, C$_1$-C$_6$ alkyl, —(C$_1$-C$_6$ alkyl)-R$^7$, C$_1$-C$_6$ alkoxy, —(C$_1$-C$_6$ alkoxy)-R$^7$, —C(O)—(C$_1$-C$_6$ alkyl), —NH$_2$, —N(C$_1$-C$_6$ alkyl)$_2$, —NH(C$_1$-C$_6$ alkyl), —(C$_1$-C$_6$ alkyl)-NH$_2$, —(C$_1$-C$_6$ alkyl)-N(C$_1$-C$_6$ alkyl)$_2$, —(C$_1$-C$_6$ alkyl)-NH(C$_1$-C$_6$ alkyl), —NH—C(O)—(C$_1$-C$_6$ alkyl), —NO$_2$, —SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —COOH, —C(O)O—(C$_1$-C$_6$ alkyl), —(C$_1$-C$_6$ alkyl)-COOH, 1-chloro-2-methyl-propyl, —C$_1$-C$_6$ thioalkyl, —(C$_1$-C$_6$ alkyl)C(O)CH$_3$, —(C$_1$-C$_6$ alkyl)OCH$_3$, C(O)NH$_2$, phenyl, benzyl, benzyloxy, morpholino, pyrrolidino, piperidine, piperizine, furan, thiophene, imidazole, tetrazole, pyrazine, pyrazolone, pyrazole, imidazole, oxazole, isoxazole, thiazole, 2-methyl-thiazole,

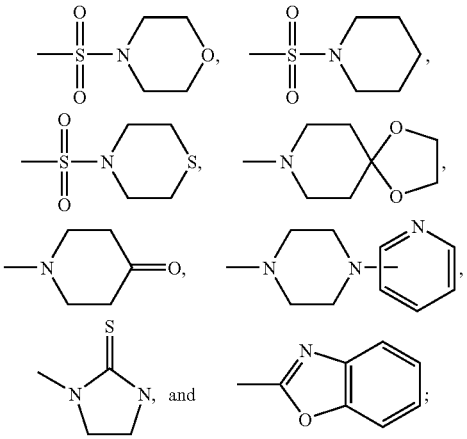

the rings of each of these $X^5$, $X^6$, $X^7$, and $X^8$ groups each being optionally substituted by from 1 to 3 substituents selected from the group consisting of halogen, —CN, —CHO, —CF$_3$, —OH, —C$_1$-C$_6$ alkyl, C$_1$-C$_6$ alkoxy, —C(O)—(C$_1$-C$_6$ alkyl), —NH$_2$, —N(C$_1$-C$_6$ alkyl)$_2$, —NH(C$_1$-C$_6$ alkyl), —NH—C(O)—(C$_1$-C$_6$ alkyl), —NO$_2$, —SO$_2$(C$_1$-C$_6$ alkyl), —SO$_2$NH(C$_1$-C$_6$ alkyl), —SO$_2$N(C$_1$-C$_6$ alkyl)$_2$, and OCF$_3$.

Examples of these embodiments include compounds wherein $X^3$ is H, $X^4$ is H, $X^5$ is —CF$_3$, $X^6$ is H, $X^7$ is H, and $X^8$ is H. Other examples include those wherein $X^3$ is H, $X^4$ is H, $X^5$ is —CH$_3$, $X^6$ is H, $X^7$ is H, and $X^8$ is —CH$_3$. In still other examples, $X^3$ is H, $X^4$ is H, $X^5$ is H, $X^6$ is Cl, $X^7$ is Cl, and $X^8$ is H.

In some embodiments, the aldehyde has the formula

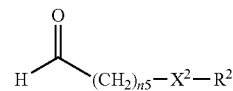

wherein $X^2$ is selected from the group consisting of —O—, —CH$_2$—, —S—, —SO—, —SO$_2$—, —NH—, —C(O)—, —NHSO$_2$—,

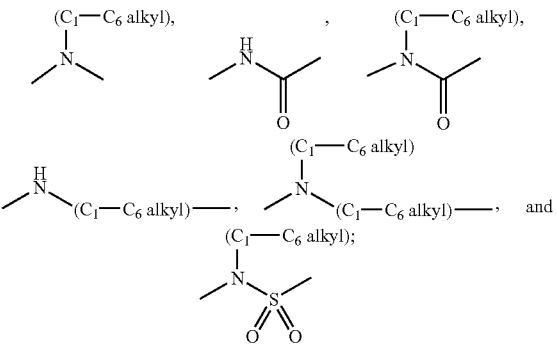

$R^2$ is a ring moiety selected from the group consisting of phenyl, pyridinyl, pyrimidinyl, furyl, thienyl and pyrrolyl, the ring moiety being substituted by a group of the formula —(CH$_2$)$_{n6}$—CO$_2$R$^8$ or a pharmaceutically acceptable bioisostere, and optionally further substituted by 1 or 2 substituents independently selected from the group consisting of halogen, —CN, —CHO, —CF$_3$, —OCF$_3$, —OH, C$_1$-C$_6$ alkyl, C$_1$-C$_6$ alkoxy, C$_1$-C$_6$ thioalkyl, —NH$_2$, —N(C$_1$-C$_6$ alkyl)$_2$, —NH(C$_1$-C$_6$ alkyl), —NH—C(O)—(C$_1$-C$_6$ alkyl), and —NO$_2$;

R$^8$ is selected from the group consisting of H and C$_1$-C$_6$ alkyl;

n$_5$ is an integer selected from 0, 1, 2, or 3; and n$_6$ is an integer selected from 0, 1, or 2.

Pharmaceutically acceptable carboxylic acid bioisosteres useful in the compounds of this invention include, but are not limited to, the following, which are bonded to R$^2$:

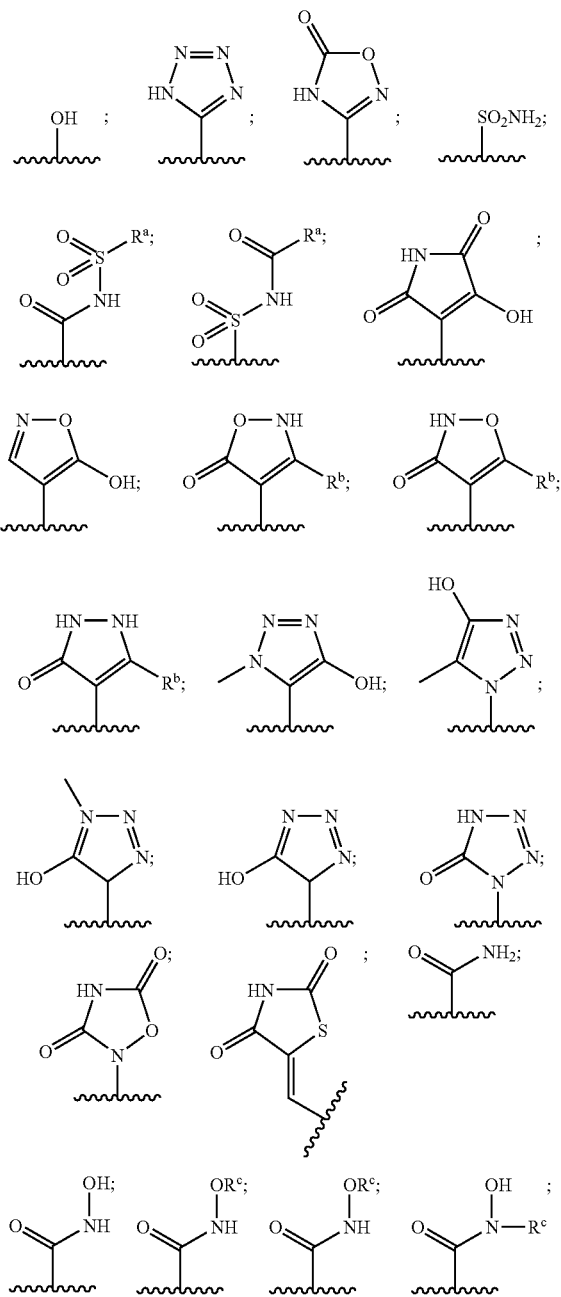

-continued

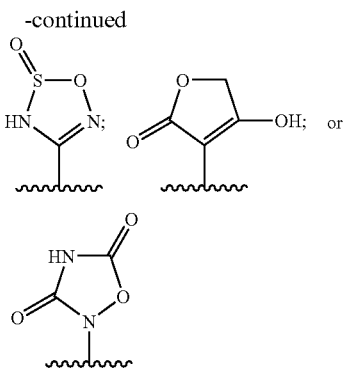

wherein R$^a$ is selected from —CF$_3$, —CH$_3$, phenyl, or benzyl, with the phenyl or benzyl groups being optionally substituted by from 1 to 3 groups selected from C$_1$-C$_6$ alkyl, C$_1$-C$_6$ alkoxy, C$_1$-C$_6$ thioalkyl, —CF$_3$, halogen, —OH, or —COOH; R$^b$ is selected from —CF$_3$, —CH$_3$, —NH$_2$, phenyl, or benzyl, with the phenyl or benzyl groups being optionally substituted by from 1 to 3 groups selected from C$_1$-C$_6$ alkyl, C$_1$-C$_6$ alkoxy, C$_1$-C$_6$ thioalkyl, —CF$_3$, halogen, —OH, or —COOH; and R$^c$ is selected from —CF$_3$ or C$_1$-C$_6$ alkyl.

In particular embodiments of the invention, the aldehyde has the formula

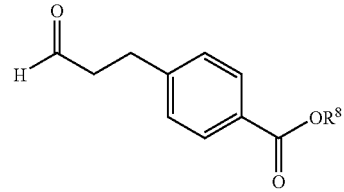

wherein R$^8$ comprises a C$_1$-C$_6$ alkyl group. After the reaction between the indole and the aldehyde has taken place, the R$^3$ group may optionally be removed to form a carboxylic acid.

According to an embodiment of the invention, the acid sensitive group bonded to the N-1 nitrogen comprises benzhydryl, the Lewis acid comprises BF$_3$, and the silicon hydride reducing agent comprises triethylsilane. The reaction may take place at approximately –20° C. In addition, trifluoroacetic acid may be added approximately 30-60 minutes after the reaction begins.

An illustrative embodiment of the present invention is shown in Scheme 1, in which an indole is alkylated at the C-3 position in the first reaction step and in a second reaction step the ester group of the C-3 substituent is cleaved to produce a carboxylic acid. The acid sensitive group in this reaction scheme is an N-benzhydryl group. In this example, boron trifluoride is the Lewis acid and is added in the form of a complex with diethyl ether (i.e., borontrifluoride diethyl etherate, BF$_3$OEt$_2$), and triethylsilane (Et$_3$SiH) is the silicon hydride reducing agent. Trifluoroacetic acid (TFA) is added 30-60 minutes after the aldehyde, indole, BF$_3$OEt$_2$ and Et$_3$SiH are combined and, therefore, after the reaction has begun.

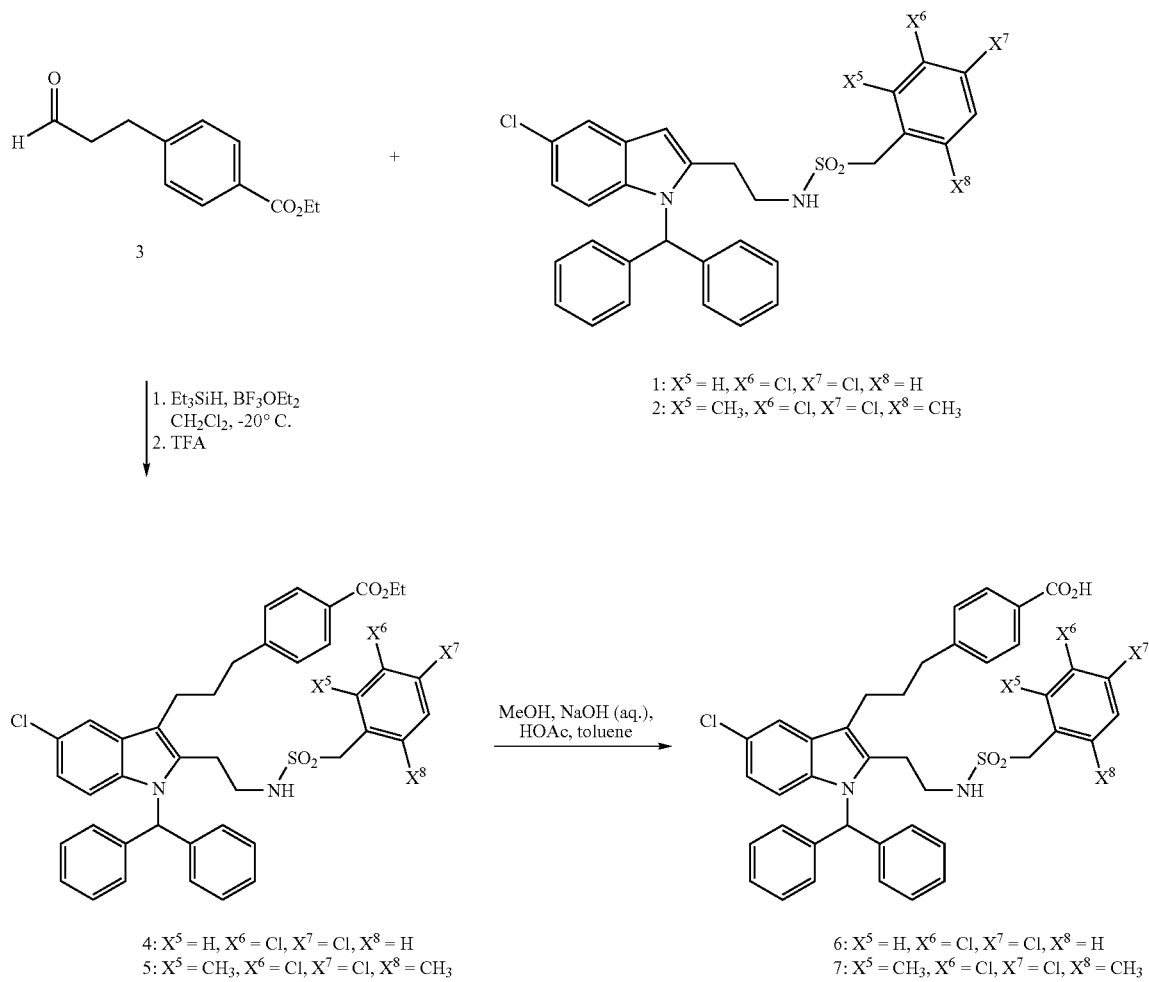

Attempts to react indole 1 with aldehydes such as 3 using trifluoroacetic acid and triethylsilane in the absence of a Lewis acid such as boron trifluoride, a Lanthanide triflate, or pentafluorophenylboronic acid result in extensive loss of the benzhydryl group at the N-1 position, which leads to almost complete removal of the group from the molecule or rearrangement to other areas of the indole structure. The combined use of a Lewis acid such as boron trifluoride, a Lanthanide triflate, or pentafluorophenylboronic acid and triethylsilane has not previously been reported as a reagent combination to alkylate the C-3 position of indoles.

Lewis acids such as boron trifluoride, Lanthanide triflates, or pentafluorophenylboronic acid are effective replacements for trifluoroacetic acid in reductive alkylation at the C-3 position of indoles containing acid-sensitive functional groups. For example, referring again to Scheme 1, treating indole 1 or 2 with aldehyde 3 in the presence of boron trifluoride and triethylsilane results in greater than 95% conversion with 80-85% selectivity to compounds 4 or 5, respectively, under favorable reaction conditions. These intermediates can conveniently be carried forward in a further reaction to hydrolyze the ester functional group to give compounds of formula 6 or 7, respectively.

In addition, the combination of a Lewis acid such as boron trifluoride with an organic acid such as trifluoroacetic acid can exert a synergistic effect on the rate of the reductive alkylation reaction. Referring to Scheme 2, a reaction performed in the absence of triethylsilane gives complete conversion of 9 to bis-alkylated dimer 10. When the reaction is performed with boron trifluoride and triethylsilane but without trifluoroacetic acid, the conversion to 10 is rapid, followed by a slow conversion of 10 to the desired product 11.

SCHEME 2

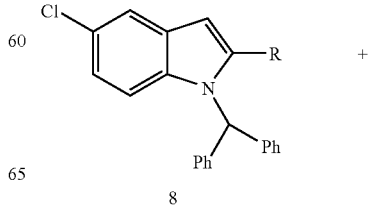

8

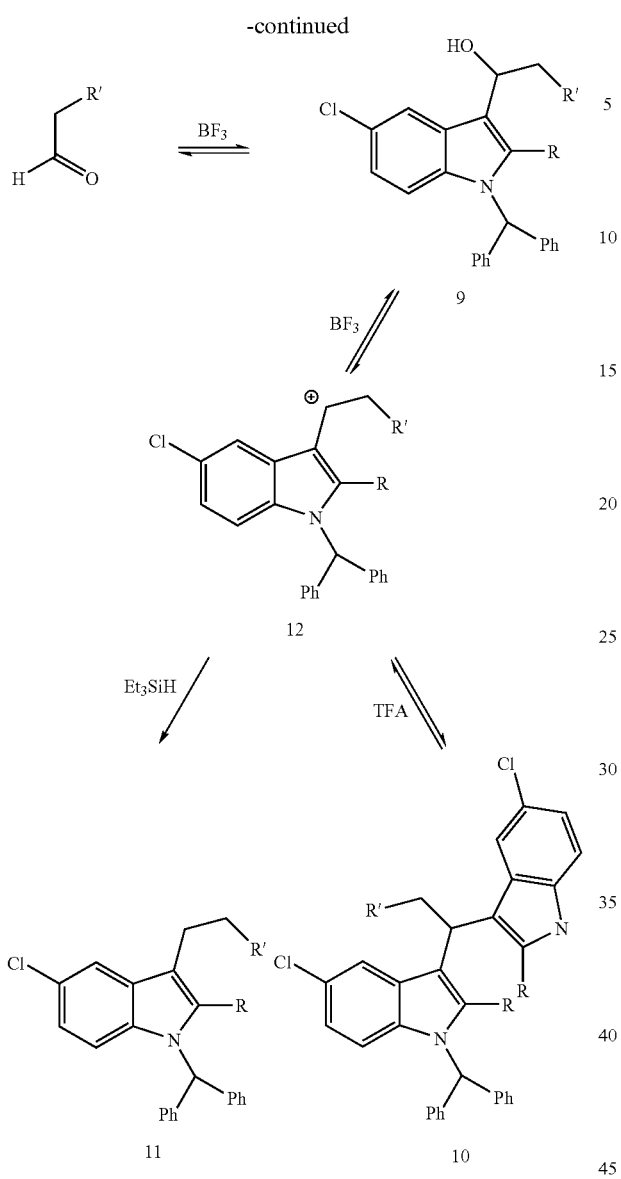

Preferred reaction conditions are an initial addition of boron trifluoride to a mixture of indole 8, aldehyde, and triethylsilane in methylene chloride as solvent, followed by addition of trifluoroacetic acid after 30-60 minutes. Under these conditions the alkylated dimer 10 is more rapidly converted to the desired product while minimizing the formation of rearranged byproducts. Preferably, the reaction of the indole and the aldehyde takes place at a temperature in the approximate range of form −30° C. to +25° C., most preferably at about −20° C.

Without intending to limit the present invention to any particular mechanism, this behavior can be mechanistically explained by the activation of the aldehyde carbonyl functional group towards alkylation of the C-3 position of the indole to form dimer 10, presumably through a cationic intermediate or transition state such as 12. Trifluoroacetic acid is more effective than boron trifluoride at activating 10 to dissociation to form 12 and starting material, with the net effect of increasing the concentration of 12, and thus the rate of its reduction, in the reaction mixture.

Particular compounds synthesized according to the invention inhibit cPLA2 activity that is required for supplying arachidonic acid substrate to cyclooxygenase-1 or -2 and 5-lipoxygenase, which in turn initiate the production of prostaglandins and leukotrienes respectively. In addition, cPLA2 activity is essential for producing the lyso-phospholipid that is the precursor to PAF. Thus these compounds may be useful in the treatment and prevention of disease states in which leukotrienes, prostaglandins or PAF are involved. Moreover, in diseases where more than one of these agents plays a role, a cPLA2 inhibitor would be expected to be more efficacious than leukotriene, prostaglandin or PAF receptor antagonists and also more effective than cyclooxygenase or 5-lipoxygenase inhibitors.

These compounds may be especially useful in the treatment of inflammatory conditions, such as arthritic and/or rheumatic disorders, including but not limited to rheumatoid arthritis, spondylo-arthropathies, gouty arthritis, osteoarthritis, systemic lupus erythematosus and juvenile arthritis. The compounds of this invention may be useful in the treatment of post-operative inflammation including that following ophthalmic surgery such as cataract surgery or refractive surgery. In addition, the compounds of the invention may be useful in the treatment of asthma.

The following examples are presented to illustrate certain embodiments of the present invention, but should not be construed as limiting the scope of this invention.

EXAMPLE 1

4-(3-{1-Benzhydryl-5-chloro-2-[2-(3,4-dichloro-phenylmethanesulfonylamino)-ethyl]-1H-indol-3-yl}-propyl)-benzoic acid N-[2-(1-Benzhydryl-5-chloro-1H-indol-2-yl)-ethyl]-C-(3,4-dichlorophenyl)-methanesulfonamide (20.0 g, 34.25 mmol), 4-(3-Oxo-propyl)-benzoic acid ethyl ester (10.5 g, 50.97 mmol), triethylsilane (12.0 g, 103.5 mmol), magnesium sulfate (0.30 g), and dichloromethane (100 mL) were combined, stirred, and cooled to −20° C. A solution of boron trifluoride diethyl etherate (3.26 g, 22.96 mmol) in dichloromethane (10 mL) was added to the reaction mixture over 2 min. After 40 min, trifluoroacetic acid (1.95 g, 17.11) was added to the reaction mixture. After three hours, the reaction mixture was filtered cold through a celite pad into aqueous sodium bicarbonate (9 g/100 mL). The organic layer was concentrated to 60 g, then methanol (100 mL) was added. The solution was concentrated to 82 g. Methanol (40 mL) and aqueous sodium hydroxide (8.2 g of a 50% solution, 102.5 mmol) were added to the mixture. The mixture was stirred and warmed to 65° C. for 6 h. After cooling the reaction mixture to room temperature, acetic acid (6.2 g, 102.5 mmol) was added and the solvent (40 g) was removed. Toluene (200 mL) and water (50 mL) were added to the mixture. The organic layer was separated and washed with water (10 mL), then concentrated to 78 g. The solid product was collected by filtration after standing overnight, then recrystallized from 10 parts of toluene to give 13.2 g (52%) of the title compound. $^1$H NMR (DMSO$_{-d6}$): δ12.80 (br.s, 1H), 7.89 (d, 2H, J=2 Hz), 7.59 (d, 1H, J=1.5 Hz), 7.53 (d, 1H, J=6 Hz), 7.48 (d, 1H, J=1.5 Hz), 7.38 (m, 9H), 7.20 (m, 5H), 6.77 (dd, 1H, J=6.9 &

1.5 Hz), 6.46 (d, 1H, J=6.9 Hz), 4.36 (s, 2H), 3.18 (m, 2H), 2.96 (m, 2H), 2.76 (m, 4H), 1.90 (m, 2H). MS: 744 MW, 99.8%.

EXAMPLE 2

4-(3-{1-Benzhydryl-5-chloro-2-[2-(2,6-dimethyl-phenylmethanesulfonylamino)-ethyl]-1H-indol-3-yl}-propyl)-benzoic acid N-[2-(1-Benzhydryl-5-chloro-1H-indol-2-yl)-ethyl]-C-(2,6-dimethyl-phenyl)-methanesulfonamide (300 g, 552 mmol), 4-(3-Oxo-propyl)-benzoic acid ethyl ester (250 g, 1.21 mol), triethylsilane (192 g, 1.66 mol), and dichloromethane (2.9 L) were combined, stirred, and cooled to −20° C. A solution of boron trifluoride etherate (55.0 g, 322 mmol) in dichloromethane (10 mL) was added to the reaction mixture over 9 min. After 35 min, trifluoroacetic acid (63 g, 553 mmol) was added to the reaction mixture. After 40 min, the reaction mixture was filtered cold through a celite pad into aqueous sodium bicarbonate (138 g/1.5 L). The organic layer was concentrated to 1.2 L g, then ethanol (1.5 L) was added. The solution was concentrated to 1.2 L. THF (450 mL) and a solution of aqueous sodium hydroxide (221 g, 2.76 mol) were added. The reaction mixture was then warmed to reflux for 30 min. The mixture was cooled to 50° C. Toluene (1.5 L), water (300 mL) and acetic acid (166 g, 2.76 mol) were added. The organic and aqueous phases were separated and the organic phase was concentrated to 1.2 L. Toluene (600 mL) was added and the mixture was concentrated to 1.2 L. The mixture was cooled to room temperature and stirred for 16 h. The solid was collected by filtration, washed with cold toluene (3×300 mL), and dried to give 317 g (81%) of the title compound.

Many variations of the present invention not illustrated herein will occur to those skilled in the art. The present invention is not limited to the embodiments illustrated and described herein, but encompasses all the subject matter within the scope of the appended claims.

What is claimed is:

1. A compound having the formula below:

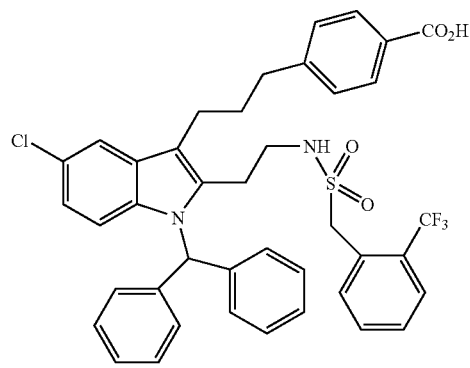

made by a method for the reductive alkylation at the C-3 position of an indole, said method comprising treating the indole with an aldehyde in the presence of a silicon hydride reducing agent selected from the group consisting of tri($C_1$-$C_4$ alkyl)silane, triphenylsilane, diphenylsilane and phenylmethylsilane, and a Lewis acid selected from the group consisting of salts of boron, aluminum, antimony or a rare earth metal and a halogen or triflate anion, and pentafluorophenyl-metallic acids in which the metal is boron, aluminum, antimony or a rare earth metal.

* * * * *